(12) United States Patent
Shi et al.

(10) Patent No.: US 8,912,345 B2
(45) Date of Patent: Dec. 16, 2014

(54) METHOD FOR PREPARING OPTICALLY PURE (−)-CLAUSENAMIDE COMPOUND

(75) Inventors: Yian Shi, Beijing (CN); Xianyou Peng, Beijing (CN); Peijun Li, Beijing (CN)

(73) Assignee: Institute of Chemistry Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/125,055

(22) PCT Filed: Nov. 4, 2011

(86) PCT No.: PCT/CN2011/001868
§ 371 (c)(1),
(2), (4) Date: Mar. 21, 2014

(87) PCT Pub. No.: WO2012/167413
PCT Pub. Date: Dec. 13, 2012

(65) Prior Publication Data
US 2014/0200355 A1  Jul. 17, 2014

(30) Foreign Application Priority Data
Jun. 10, 2011  (CN) .......................... 2011 1 0155173 7

(51) Int. Cl.
*C07D 207/273* (2006.01)
(52) U.S. Cl.
CPC ................................. *C07D 207/273* (2013.01)
USPC ....................................................... 548/544
(58) Field of Classification Search
CPC .................................................. C07D 207/273
USPC ....................................................... 548/544
See application file for complete search history.

(56) References Cited

U.S. PATENT DOCUMENTS

| 4,731,456 A * | 3/1988 | Hartwig ......................... 548/544 |
| 5,132,433 A * | 7/1992 | Huang et al. .................. 548/544 |
| 2003/0207935 A1 | 11/2003 | Zhang et al. |

FOREIGN PATENT DOCUMENTS

| CN | 86107090 A | 4/1987 |
| CN | 1050185 A | 3/1991 |
| CN | 1040440 C | 10/1998 |
| CN | 1345721 A | 4/2002 |
| EP | 0414020 A2 | 2/1991 |

OTHER PUBLICATIONS

Li et al. "Synthesis of N-substituted Clausenamide Analogs." Eur. J. Med. Chem. 2010, 45, 5531-5538.*
Zhou et al. "Study on the Synthesis of Metabolite of Clausenamide (CM1)." Chinese Chem. Lett. 2002, 13, 528-530.*
Yakura et al. "Formal Total Synthesis of Clausenamide." Synlett 1991, 5, 343-344.*
Becker et al. "Synthesis of Single-Enantiomer 6-Hydroxy-7-phenyl-1,4-oxazepan-5-ones." Synthesis 2005, 15, 2549-2561.*
Wang, Bin et al., "A Diacetate Ketone-Catalyzed Asymmetric Epoxidation of Olefins", The Journal of Organic Chemistry, vol. 74, No. 10, May 15 2009, pp. 3986-3989.
ISA State Intellectual Property Office of China, International Search Report of PCT/CN2011/001868, WIPO, Mar. 22, 2012, 4 pages.

* cited by examiner

*Primary Examiner* — Joseph Kosack
*Assistant Examiner* — Amanda L Aguirre
(74) *Attorney, Agent, or Firm* — Alleman Hall McCoy Russell & Tuttle LLP

(57) ABSTRACT

Disclosed in the present invention is a method for preparing a (−)-clausenamide compound of formula (I), comprising: firstly, catalyzing the asymmetrical epoxidation of trans-cinnamate using a chiral ketone derived from fructose or a hydrate thereof as a catalyst, and then subjecting the product to amidation, oxidation, cyclization and reduction successively to finally obtain the optically pure (−)-clausenamide compound of formula (I).

10 Claims, 1 Drawing Sheet

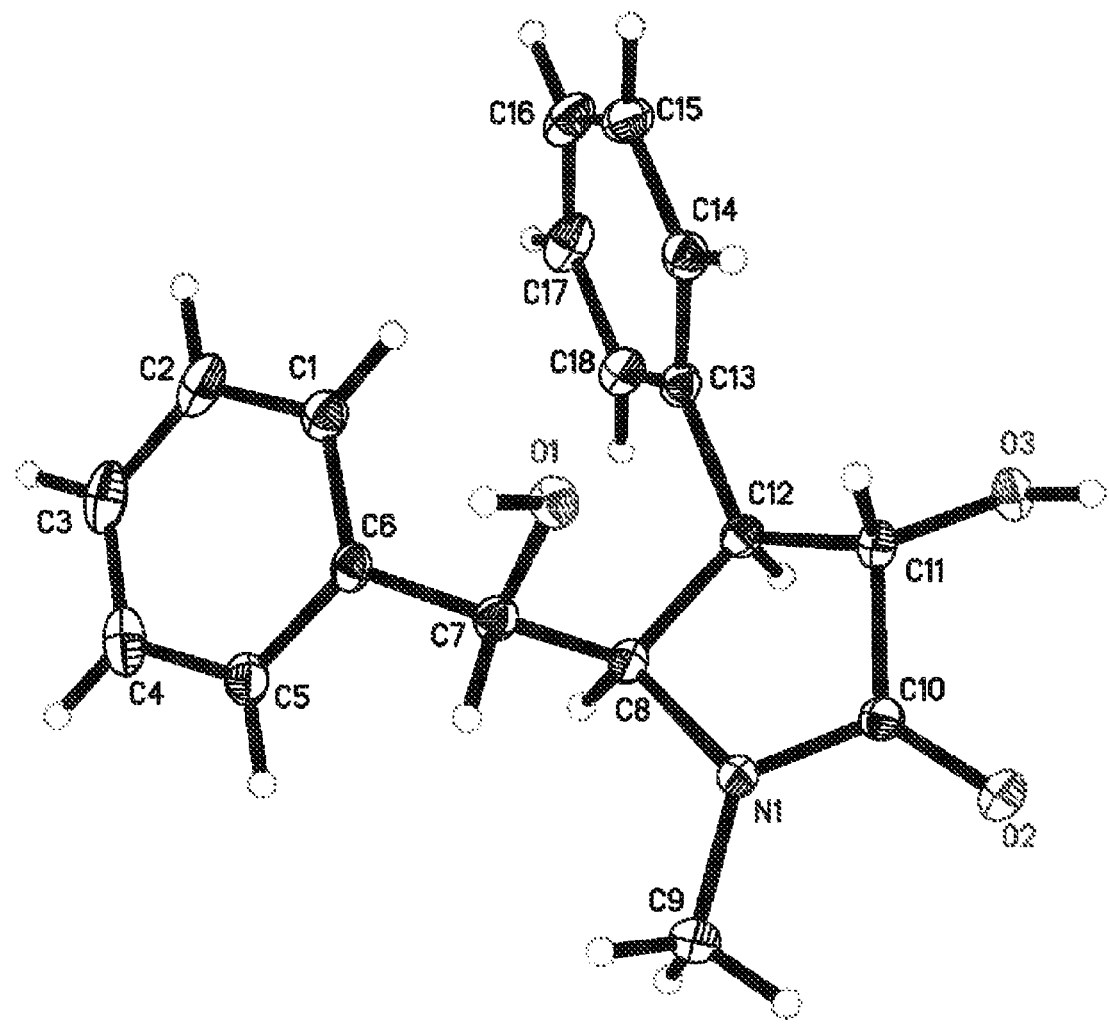

METHOD FOR PREPARING OPTICALLY PURE (−)-CLAUSENAMIDE COMPOUND

CROSS-REFERENCE TO RELATED APPLICATIONS

This is the U.S. National Phase of International PCT Application Serial No. PCT/CN2011/001868, entitled "Method for Preparing Optically Pure (−)-Clausenamide Compound", filed on Nov. 4, 2011, which claims priority to Chinese Utility Model Application No. 2011101551737, filed Jun. 10, 2011, both of which are hereby incorporated by reference in their entirety for all purposes.

FIELD OF THE INVENTION

The present invention relates to a method for preparing optically pure (−)-clausenamide compounds.

BACKGROUND

Clausenamide compounds are a species of amide compounds possessing physiological activity, which are extracted from leaves, stems, and fruits of lausena Lansium (Lour) skeels, a folk herbal medicine in South of China. The group led by Professor Huang, Liang of Institute of Materia Medica, Chinese Academy of Medical Sciences & Peking Union Medical College did a lot of work on extracting active ingredients in leaves of lausena Lansium (Lour) skeels, achieved very abundant research results, and defined compounds with a structure of general formula (a) as clausenamide. To date, people have separated almost twenty species of clausenamide compounds from lausena Lansium (Lour) skeels. Then, as shown in researches for biological activities of these compounds, optically pure (−)-clausenamide has an evident effect on improving intelligence, resisting acute cerebral ischemia, and delaying tissue aging, which thereby is promising for treating senile dementia. Additionally, it was also found in the researches that the effect of optically pure (−)-clausenamide is 50 times higher than that of Piracetam, a marketed drug. However, clausenamide obtained by natural separation is a racemate, and (+)-clausenamide not only has no positive effect, but has a certain inhibiting effect. Therefore, it is important to obtain a method for inhibiting the generation of (+)-clausenamide while preparing optically pure (−)-clausenamide in large amount. After clausenamide was isolated, scientists have proposed a lot of synthetic routes, such as synthetic methods of racemic clausenamide respectively disclosed by EP0414020, CN86107090, CN90107145.5, and CN90107144.7. Furthermore, in order to obtain optically pure (−)-clausenamide, some scientists utilized chiral separation methods, such as the chiral separation method disclosed by CN 1345721A. A typical chiral separation method comprises: (1) firstly, synthesizing clausenamidone, then obtaining optically pure (−)-clausenamide by using a chiral separation method; (2) using menthol derivates as substrates of a chiral source to control Darzens reaction so as to obtain chiral intermediates; and the like.

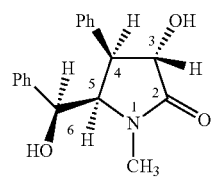

(a)

The current methods of preparing optically pure (−)-clausenamide need to perform chiral separation or have some post-treatment problems such as chromatographic column purification, etc., which limits the industrialized production of optically pure (−)-clausenamide. Therefore, it is desired for a method of preparing optically pure (−)-clausenamide which has no need for chiral separation and has a convenient post-treatment, to achieve the industrialized requirements of optically pure (−)-clausenamide.

SUMMARY

The object of the present invention is to provide a method of preparing an optically pure (−)-clausenamide compound represented by formula (I), the method can prepare a (−)-clausenamide compound represented by formula (I) in batch.

The method for preparing a (−)-clausenamide compound represented by formula (I) provided by the present invention comprises the following steps:

(1) in the presence of an oxidant and a catalyst, trans-cinnamate represented by formula (II) is converted to (2S, 3R)-epoxy cinnamate represented by formula (III) through asymmetric epoxidation reaction; the catalyst is fructose-derived chiral ketone represented by formula (IV) or a hydrate of fructose-derived chiral ketone represented by formula (V);

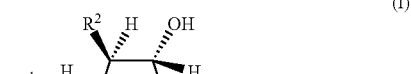

(I)

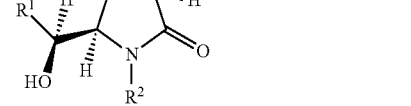

(II)

(III)

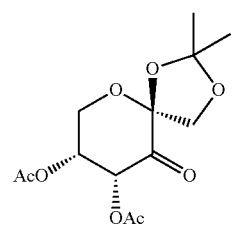

(IV)

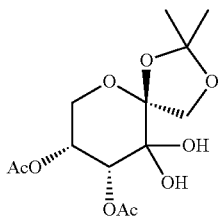

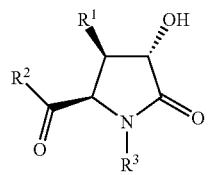

wherein, both R¹ and R² are any one selected from the group consisting of phenyl, o-methoxyphenyl, m-methoxyphenyl, p-methoxyphenyl, o-methylphenyl, m-methylphenyl, p-methylphenyl, p-fluorophenyl, p-chlorophenyl, p-bromophenyl, o-fluorophenyl, o-chlorophenyl, o-bromophenyl, 3,4,5-trimethoxyphenyl, p-nitrophenyl, and α-naphthyl; R³ is any one selected from the group consisting of hydrogen, methyl, benzyl, p-methoxybenzyl, and hydroxymethyl; and R⁴ is any one selected from the group consisting of methyl, ethyl, n-propyl, isopropyl, n-butyl, t-butyl, cyclohexyl, and benzyl;

(2) in the presence of an alkaline compound, amidation reaction takes place between (2S,3R)-epoxy cinnamate represented by formula (III) and a compound represented by formula (VI), to obtain a compound represented by formula (VII);

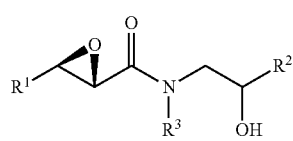

wherein, the definitions of $R^1$, $R^2$ and $R^3$ are the same as those in formula (I);

(3) in the presence of ruthenium trichloride and the oxidant, the compound represented by formula (VII) is converted to a compound represented by formula (VIII) through oxidation reaction;

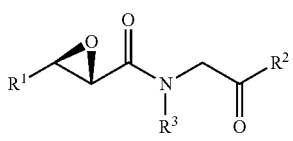

wherein, the definitions of $R^1$, $R^2$ and $R^3$ are the same as those in formula (I);

(4) in the presence of an alkaline compound, the compound represented by formula (VIII) is converted to (−)-clausenamidone compound represented by formula (IX) through cyclization reaction;

wherein, the definitions of $R^1$, $R^2$ and $R^3$ are the same as those in formula (I);

(5) the (−)-clausenamidone compound represented by formula (IX) is converted to a (−)-clausenamide compound represented by the formula (I) through reduction reaction.

In the preparation method described above, the oxidant described in step (1) and step (3) can be any one selected from the group consisting of sodium perbromate, sodium hypochlorite, sodium periodate, potassium monopersulfate, potassium peroxymonosulfate, and hydrogen peroxide.

In the preparation method described above, in step (1), the ratio of mole fractions of trans-cinnamate represented by formula (II) to the oxidant to the catalyst can be 1:(2.5-10): (0.05-1.0), specifically can be 1:5:0.3; the temperature of the asymmetrical epoxidation reaction can be −15° C. to 50° C., specifically can be −5° C., and the reaction time can be 5 hours to 24 hours, specifically can be 5 hours.

In the preparation method described above, the alkaline compound described in step (2) and step (4) can be any one selected from the group consisting of sodium methoxide, sodium ethoxide, sodium tert-butoxide, potassium tert-butoxide, sodium carbonate, potassium carbonate, sodium bicarbonate, potassium bicarbonate, sodium hydroxide, potassium hydroxide, lithium hydroxide, sodium acetate, and potassium acetate.

In the preparation method described above, the ratio of mole fractions of (2S,3R)-epoxy cinnamate represented by formula (III) to the compound represented by formula (VI) in step (2) can be 1:(1.1-1.2), specifically can be 1:1.1, and the ratio of mole fractions of the alkaline compound to (2S,3R)-epoxy cinnamate represented by formula (III) can be 1:(0.10-1.0), specifically can be 1:0.3; the temperature of the amidation reaction can be −20° C. to 40° C., specifically can be −20° C. or 40° C.; and the reaction time is 0.5 hours to 3 hours, specifically can be 0.5 hours or 2 hours.

In the preparation method described above, the ratio of mole fractions of the compound represented by formula (VII) to the oxidant to ruthenium trichloride in step (3) can be 1:(1-10):(0.03-0.30), specifically can be 1:2:0.03 or 1:2:0.04; and the temperature of the oxidation reaction can be −20° C. to 90° C., specifically can be 77° C. to 80° C.; and the reaction time can be 0.5 hours to 24 hours, specifically can be 5 hours.

In the preparation method described above, the solvent of the cyclization reaction in step (4) can be an aqueous solution of the alkaline compound; in the aqueous solution, the mass percentage of the alkaline compound can be 0.5%-5%; the temperature of the cyclization reaction can be 10° C. to 90° C., specifically can be 55° C.; and the time of the cyclization reaction can be 0.2 hours to 2 hours, specifically can be 2 hours.

In the preparation method described above, step (1) and/or step (3) can further comprise the step of adding an additive; the additive can be at least one of a phase transfer catalyst, an aqueous solution of disodium ethylenediamine tetraacetic acid, and the alkaline compound; the molar concentration of the aqueous solution of disodium ethylenediamine tetraacetic acid can be 0 to 0.001 mol/L, but not 0, such as 0.0001 mol/L or 0.0005 mol/L; the phase transfer catalyst can be any one selected from the group consisting of benzyl triethyl ammonium chloride, tetrabutyl ammonium bromide, tetrabutyl ammonium chloride, tetrabutyl ammonium iodide, tetrabutyl ammonium bisulfate, trioctyl methyl ammonium chloride, dodecyl trimethyl ammonium chloride, and tetradecyl trimethyl ammonium chloride.

In the preparation method described above, a reductant of the reduction reaction in step (5) is sodium borohydride; the ratio of mole fractions of (−)-clausenamidone compound represented by formula (IX) to the reductant is 1:(1.0-2.0), specifically can be 1:2; the temperature of the reduction reaction is −20° C. to 40° C., specifically can be 25° C. or 30° C.; and the time of the reduction reaction is 0.5 hours to 3 hours, specifically can be 1 hour or 3 hours.

In the preparation method described above, all of the solvents of the reactions in step (1), step (2), step (3), step (4), and step (5) can be at least one selected from the group consisting of ethers solvent, alcohols solvent, esters solvent, halogenated alkanes solvent, $C_5$-$C_{10}$ alkanes solvent, amides solvent, nitriles solvent, and water; the ethers solvent is any one selected from the group consisting of ethyl ether, dipropyl ether, dibutyl ether, methyl t-butyl ether, 1,3-dioxane, 1,4-dioxane, tetrahydrofuran, dimethoxymethane, ethylene glycol monomethyl ether, ethylene glycol dimethyl ether, ethylene glycol monoethyl ether, ethylene glycol diethyl ether, and t-butyl methyl ether; the alcohols solvent is any one selected from the group consisting of methanol, ethanol, n-propyl alcohol, isopropyl alcohol, n-butyl alcohol, sec-butyl alcohol, t-butyl alcohol, and glycol; the esters solvent is any one selected from the group consisting of ethyl acetate, methyl acetate, propyl acetate, t-butyl acetate, and ethyl formate; the halogenated alkanes solvent is any one selected from the group consisting of dichloromethane, trichloromethane, and 1,2-dichloroethane; the $C_5$-$C_{10}$ alkanes solvent is any one selected from the group consisting of n-pentane, n-hexane, n-heptane, toluene, and dimethylbenzene; the amides solvent is selected from the group consisting of N,N-dimethylfomamide or N,N-dimethylacetamide; and the nitriles solvent is selected from the group consisting of acetonitrile or propionitrile.

BRIEF DESCRIPTION OF THE DRAWINGS

FIG. 1 is a monocrystal X-ray diffraction diagram of (−)-clausenamide.

DETAILED DESCRIPTION OF PREFERRED EMBODIMENT

All of the experimental methods used in the following examples are common methods, unless otherwise specified.

All of the materials, reagents, and the like used in the following examples are commercially available, unless otherwise specified.

The molecular formula of potassium peroxymonosulfate used in the following examples of the present invention is $2KHSO_5 \cdot KHSO_4 \cdot K_2SO_4$, which is purchased from Beijing Ouhe Technology Co., Ltd under the trade name of Oxone®.

Example 1

The Preparation of (−)-Clausenamide (1) The preparation of (+)-(2S,3R)-epoxy t-butyl cinnamate

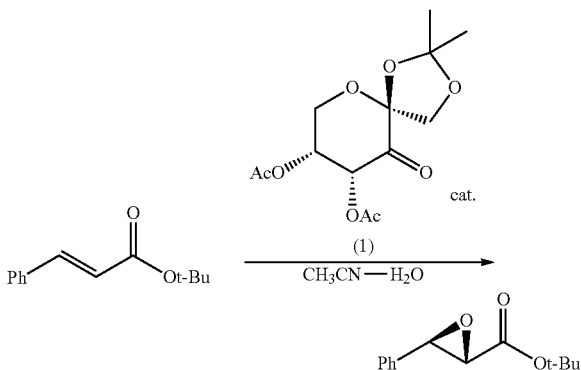

The reaction equation is shown as above, and in the equation, Ph is phenyl; t-Bu is t-butyl; and Ac is acetyl.

Trans-t-butyl cinnamate (1.0 mol, 204.0 g) dissolved in 5.0 L acetonitrile was added to 50 L reaction kettle equipped with a mechanical stirrer rinsed by deionized water, dissolved in 2.5 L acetonitrile to obtain fructose-derived chiral ketone represented by formula (1) having a concentration of 0.12M (wherein the ratio of mole fractions of trans-t-butyl cinnamate to fructose-derived chiral ketone represented by formula (1) is 1:0.30), and tetra-n-butyl ammonium bisulfate (0.06 mol, 20.0 g) was added, then an aqueous solution containing 5.0 L $1 \times 10^{-4}$ M disodium ethylenediamine tetraacetic acid was added; a cooling liquid was led into the interlayer of the reaction kettle, and the temperature inside the reaction kettle was adjusted to −5° C.; a mixture of 3.08 kg potassium peroxymonosulfate (Oxone®, the ratio of mole fractions of trans-t-butyl cinnamate to potassium peroxymonosulfate is 1:5) grinded by a herbal medicine grinder and 1.30 kg $NaHCO_3$ was added in batch while stirring, and it took about 4.5 hours to finish the addition of the above mixture, after which the reaction mixture was continuously stirred and reacted under this condition, and gas chromatography was used at a fixed time to detect the reaction state (gas chromatography monitoring condition: column: DM-5, temperature of vaporizing chamber: 250° C., column temperature: 170° C., temperature of hydrogen flame ionization detector: 250° C., column pressure: 30 psi, product retention time: 3.4 min, stock retention time: 3.0 min); after reacting for 5 hours, 5.0 L water-diluted reaction liquid was added, and the reaction was extracted with 5.0 L ethyl acetate; water phase was transferred into 20 L reaction kettle, and 2.5 L ethyl acetate was added to perform an extraction; the organic phases were combined, and washed with 5.0 L saturated solution of sodium chloride; the organic phase was fully dried with a suitable amount of anhydrous sodium sulfate, then filtered, the solvent was removed by reduced pressure distillation, then epoxy trans-t-butyl cinnamate crude product was obtained (the content of gas phase: 90%, enantiomeric excess was determined by high performance liquid chromatography: 94.9%, Chiralcel OD-H, column temperature 25° C., the volume ratio of n-hexane:isopropyl alcohol is 99:1, the flow rate is 1.0 mL/min, $t_1$=8.27 min, $t_2$=10.29 min; the epoxy trans-t-butyl cinnamate crude product obtained by dissolving 150 mL ethanol and 150 mL n-hexane, was then placed at 0° C. to −20° C. to perform a recrystallization, and 146.2 g optically pure (+)-(2S,3R)-epoxy t-butyl cinnamate was obtained, the yield is 66.5%, the content of gas phase is 98.8%, enantiomeric excess is 99.3%, $[\alpha]_D^{20}$=+124 (c 1.0, $CHCl_3$).

$^1$H NMR [400 MHz, $CDCl_3$] δ 7.40-7.31 (m, 3H), 7.31-7.27 (m, 2H), 4.02 (s, 1H), 3.41 (s, 1H), 1.52 (s, 9H); $^{13}$C NMR [100 MHz, $CDCl_3$] δ 167.43, 135.56, 129.08, 128.81, 126.09, 82.89, 57.84, 57.66, 28.23.

(2) The Preparation of (+)-(2S,3R)—N-methyl-N-(β-hydroxylphenethyl)-β-phenyl glycidic acid amide

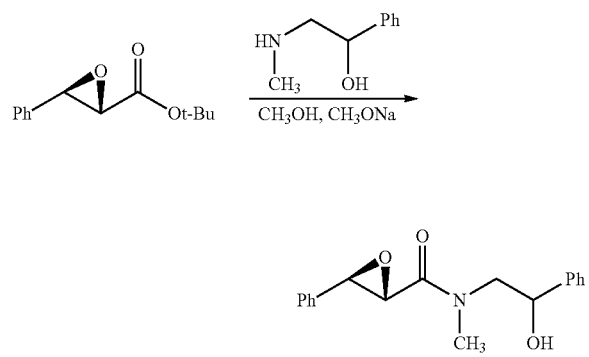

The reaction equation is shown as above, and in the equation, Ph is phenyl; and t-Bu is t-butyl;

150.0 g optically pure (+)-(2S,3R)-epoxy t-butyl cinnamate obtained in step (1) and 113.4 g N-methyl-β-hydroxyphenethylamine were added to 500 mL reactor (wherein the ratio of mole fractions of (+)-(2S,3R)-epoxy t-butyl cinnamate to N-methyl-β-hydroxyphenethylamine is 1:1.1), then 200 mL absolute methanol was added to dissolve them, and 11.0 g sodium methoxide (the ratio of mole fractions of sodium methoxide to (+)-(2S,3R)-epoxy t-butyl cinnamate is 1:0.3) was slowly added while stirring; the reaction temperature was controlled to be 0° C., the reaction state was monitored at a fixed time by gas chromatography (the monitoring condition is the same as that in step (1)), until the stock was fully consumed; after 0.5 hours, the reaction was finished, methanol was removed by reduced pressure distillation, and the reaction was extracted by about 2.0 L ethyl acetate; the organic phase was sequentially washed by 500 mL saturated sodium bicarbonate and 500 mL saturated saline solution; the organic phase was dried by anhydrous sodium sulfate, filtrated, and ethyl acetate was removed by reduced pressure distillation, then a syrupy liquid was obtained, 50 mL ethyl ether then was added and stirred until the solid was precipitated, filtrated, and 156.0 g yellow solid, i.e., (+)-(2S,3R)—N-methyl-N-(β-hydroxylphenethyl)-β-phenyl glycidic acid amide, was obtained, the yield is 77%;

(3) The Preparation of (+)-(2S,3R)—N-methyl-N-(α-acetophenonyl)-β-phenyl glycidic acid amide

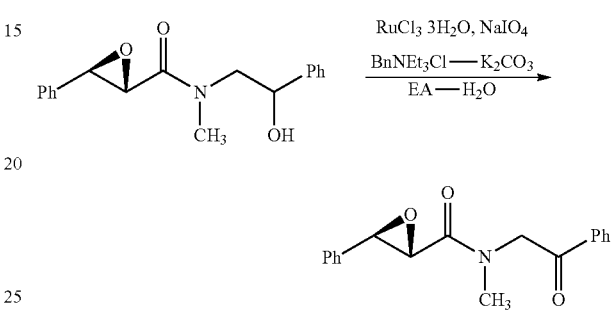

The reaction equation is shown as above, and in the equation, Ph is phenyl; Bn is benzyl; Et is ethyl; and EA is ethyl acetate;

156.0 g (+)-(2S,3R)—N-methyl-N-(β-hydroxylphenethyl)-β-phenyl glycidic acid amide obtained in step (2), 6.0 g benzyl triethyl ammonium chloride, 224.7 g sodium periodate, 10.87 g potassium carbonate, and 420 mL ethyl acetate and 420 mL double distilled water were added to 3 L double-mouth bottle with mechanical agitation and reflux condensing tubes, the reaction mixture is present in solid-liquid two phases, then 4.1 g trihydrated ruthenium trichloride was added while stirring (in this system, the ratio of mole fractions of (+)-(2S,3R)—N-methyl-N-(β-hydroxylphenethyl)-β-phenyl glycidic acid amide to sodium periodate to trihydrated ruthenium trichloride is 1:2:0.03), after about 5 minutes, the reaction mixture became a black (or deep green) suspension from a white suspension, and was dramatically exothermal, the exothermal heat made the reaction mixture automatically reflux (the temperature is 77° C. to 80° C.); the reaction state was monitored at a fixed time by thin layer chromatography (Rf=0.20, the volume ratio of petroleum ether:ethyl acetate is 2:1), and 5 h after the reaction, the stock was fully consumed, then the post-treatment was performed; the post-treatment method was to filtrate the deep green reaction liquid with a sand core funnel filled with diatomite, the filtrate was collected, washed to be colourless or faint yellow that was nearly colourless with saturated sodium sulfite aqueous solution, and the organic phases were combined, then the organic phase was washed with saturated saline solution, dried by anhydrous magnesium sulfate, magnesium sulfate was removed by filtration, the organic solvent was removed by reduced pressure distillation, and 132.5 g faint yellow slabby crude product was obtained, the yield is 85%; ethyl ether was added to this slabby crude product and stirred, then solid was precipitated, and 80.5 g white solid, i.e., (+)-(2S,3R)—N-methyl-N-(α-acetophenonyl)-β-phenyl glycidic acid amide, was obtained, the yield is 52%;

(4) The Preparation of (−)-clausenamidone

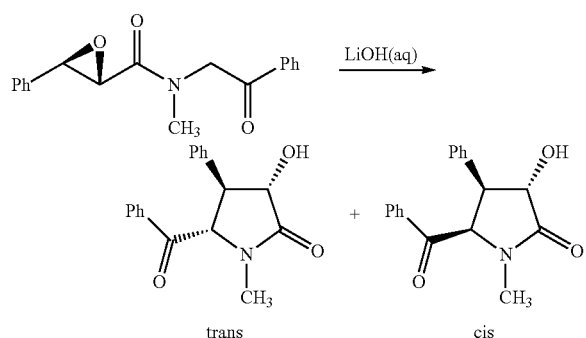

trans     cis

The reaction equation is shown as above, and in the equation, Ph is phenyl; trans is referred to trans-(+)-clausenamidone; cis is referred to cis-(−)-clausenamidone;

60.0 g (+)-(2S,3R)—N-methyl-N-(α-acetophenonyl)-β-phenyl glycidic acid amide obtained in step (3) was added to 2.0 L single mouth bottle equipped with a mechanical stirrer, which was placed in a 55° C. water bath, 800 mL monohydrated lithium hydroxide aqueous solution with a mass percentage of 1.5% was added (the preparation method: 15.0 g monohydrated lithium hydroxide was dissolved to 1.0 L double distilled water), after stirring for about 10 minutes, white solid was precipitated, and the reaction liquid was continuously stirred for 2 hours, after the reaction was finished, the reaction bottle was immediately placed into a refrigerator (−20° C.) to freeze, after about 1 h, filtrated to obtain white solid, after NMR analysis, it was found out that cis:trans >20:1, and this cis- and trans-mixture was dissolved with ethyl acetate, then placed in a low temperature of −20° C. to precipitate a crystal, filtrated to obtain a white crystal, i.e., optically pure (−)-clausenamidone, after dried, 48.5 g crystal was obtained, the yield is 80%, the melting point is 189-191° C., and the optical value is $[\alpha]_D^{20}=-355°$ (c 0.29, MeOH).

The melting point: 189-191° C.; 1H NMR [400 MHz, CDCl3] δ 7.54-7.00 (10H), 5.39 (d, J=9.19 Hz), 4.92 (d, J=9.19 Hz), 3.86 (dd, J=9.19 Hz), 2.89 (3H, s, NCH3); 13C NMR [100 MHz, CDCl3] 197.5, 175.2, 134.4, 133.7, 128.8, 128.6, 128.4, 128.1, 65.2, 51.6, 29.8;

(5) The preparation of (−)-clausenamide

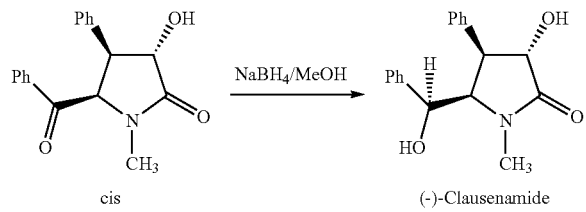

cis     (−)-Clausenamide

The reaction equation is shown as above, and in the equation, Ph is phenyl;

50.6 g (−)-clausenamidone obtained in step (4) was placed into 3 L single mouth round-bottomed flask, then 2.4 L absolute methanol was added, the reaction mixture was cooled to 0° C., and 12.9 g sodium borohydride was added under stirring by the mechanical agitation (the ratio of mole fractions or ratio of mass fractions of (−)-clausenamidone to sodium borohydride is 1:2); after 0.5 hours, the temperature was increased to 25° C. and the stirring last for 3 hours; after the reaction was finished, the pH value of the reaction liquid was adjusted to 3 with 2M hydrochloric acid aqueous solution, the solvent was removed by reduced pressure distillation, and a large amount of white solid materials (in addition to the target products, some salt impurities were also included) were obtained; 2.0 L ethyl acetate and 1.0 L water were added to make the solid materials dissolve, which was then extracted, the organic phase was sequentially washed by 500 mL saturated sodium bicarbonate aqueous solution and 500 mL saturated saline solution, then dried by anhydrous magnesium sulfate, filtrated to remove magnesium sulfate, the organic solvent was removed by reduced pressure distillation, and white clausenamide crude product was obtained; then the clausenamide crude product was dissolved with ethyl acetate, and placed into a low temperature of −20° C. to perform recrystallization, after filtrated and dried, 45.2 g obtained white crystal is optically pure (−)-clausenamide, the yield is 89%, the melting point is 147-149° C., the optical rotation is $[\alpha]D20=-157°$ (c 0.21, MeOH); the monocrystal X-ray diffraction testing result of the resultant (−)-clausenamide obtained by X-ray monocrystal diffractometer-1 [RAXIS-RAPID] is shown in FIG. 1, indicating that the absolute configuration of the prepared clausenamide is (3S,4R,5R,6S), which has a left optical activity. 1H NMR [400 MHz, DMSO] δ 7.26 (8H, m, 8H), 6.63-6.66 (2H), 5.45 (1H), 5.34 (J=6.3 Hz), 4.64 (1Hs), 4.26 (J=8.4, 6.4 Hz), 3.85 3.01 (s, 3H); $^{13}$C NMR [100 MHz, CDCl3] δ 178.5, 134.5, 133.3, 128.8, 128.7, 128.6, 128.4, 128.1, 72.1, 71.6, 66.2, 30.4.

INDUSTRIAL APPLICATIONS

The preparation method provided by the present invention has the following advantages:

(1) the present invention utilizes trans-cinnamate represented by formula (II) as a stock and cheap hydrate of fructose-derived chiral ketone represented by formula (V) or fructose-derived chiral ketone represented by formula (IV) as catalysts, adds oxidant to perform an asymmetric epoxidation reaction and prepares (2S,2R)-epoxy cinnamate intermediate represented by formula (III);

(2) the present invention screens the desired oxidant for the oxidation preparation of the compound represented by formula (VIII) from the compound represented by formula (VII), the selected oxidation method is more environmentally friendly, and the post-treatment is more convenient.

(3) the present invention detailly optimizes the method of the cyclization preparation of the (−)-clausenamidone compound represented by formula (IX) from the compound represented by formula (VIII), and the efficiency of cyclization method is greatly improved and enhanced, and after cyclization, the content ratio of cis-(−)-clausenamidone to trans-(+)-neoclausenamidone is greater than 5:1.

(4) the purpose of the preparation method of the present invention is to realize the industrialized preparation of an optically pure (−)-clausenamide compound, and in the post-treatment process, the target product can be obtained by using methods, such as extraction, filtration or recrystallization, etc., which are easily achievable in the industry.

(5) all of the reactions in the present invention can be carried out in a enlarged amount, and the production can be enlarged from a lab-scale to an industrialized bench-scale, pilot-plant scale and a large scale, so as to provide a convenient method of synthesizing an optically pure (−)-clausenamide compound, and to provide a good method for drug screening.

The invention claimed is:

1. A method for preparing a (−)-clausenamide compound represented by formula (I), comprising the following steps:
   (1) in the presence of an oxidant and a catalyst, trans-cinnamate represented by formula (II) is converted to (2S,3R)-epoxy cinnamate represented by formula (III) through asymmetric epoxidation reaction; the catalyst is fructose-derived chiral ketone represented by formula (IV) or a hydrate of fructose-derived chiral ketone represented by formula (V);

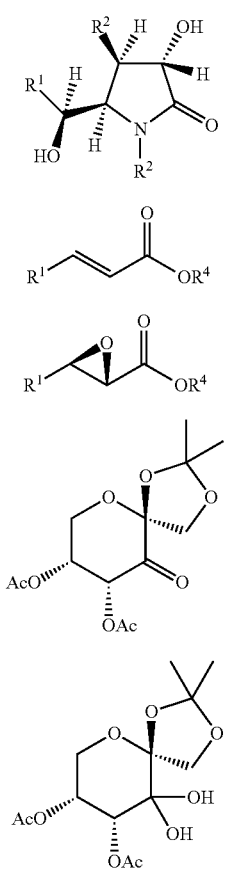

wherein, both $R^1$ and $R^2$ are any one selected from the group consisting of phenyl, o-methoxyphenyl, m-methoxyphenyl, p-methoxyphenyl, o-methylphenyl, m-methylphenyl, p-methylphenyl, p-fluorophenyl, p-chlorophenyl, p-bromophenyl, o-fluorophenyl, o-chlorophenyl, o-bromophenyl, 3,4,5-trimethoxyphenyl, p-nitrophenyl, and α-naphthyl; $R^3$ is any one selected from the group consisting of hydrogen, methyl, benzyl, p-methoxybenzyl, and hydroxymethyl; $R^4$ is any one selected from the group consisting of methyl, ethyl, n-propyl, isopropyl, n-butyl, t-butyl, cyclohexyl, and benzyl; and Ac is acetyl;

(2) in the presence of an alkaline compound, amidation reaction takes place between (2S,3R)-epoxy cinnamate represented by formula (III) and a compound represented by formula (VI), to obtain a compound represented by formula (VII);

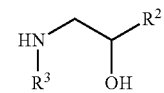

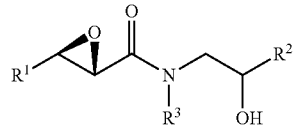

wherein, the definitions of $R^1$, $R^2$ and $R^3$ are the same as those in formula (I);

(3) in the presence of ruthenium trichloride and the oxidant, the compound represented by formula (VII) is converted to a compound represented by formula (VIII) through oxidation reaction;

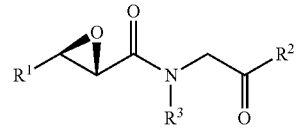

wherein, the definitions of $R^1$, $R^2$ and $R^3$ are the same as those in formula (I);

(4) in the presence of an alkaline compound, the compound represented by formula (VIII) is converted to (−)-clausenamidone represented by formula (IX) through cyclization reaction;

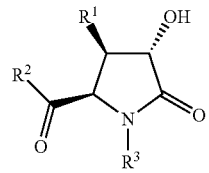

wherein, the definitions of $R^1$, $R^2$ and $R^3$ are the same as those in formula (I);

(5) the (−)-clausenamidone represented by formula (IX) is converted to the (−)-clausenamide represented by the formula (I) through reduction reaction.

2. The method of claim 1, wherein the oxidant of step (1) and step (3) is any one selected from a group consisting of sodium perbromate, sodium hypochlorite, sodium periodate, potassium monopersulfate, potassium peroxymonosulfate, and hydrogen peroxide.

3. The method of claim 1, wherein in step (1), the ratio of mole fractions of the trans-cinnamate represented by formula (II) to the oxidant to the catalyst is 1:(2.5-10):(0.10-1.0); a temperature of the asymmetric epoxidation reaction is −15° C. to 50° C.; and a reaction time is 5 hours to 24 hours.

4. The method of claim 3, wherein the alkaline compound of step (2) and step (4) is any one selected from a group consisting of sodium methoxide, sodium ethoxide, sodium tert-butoxide, potassium tert-butoxide, sodium carbonate, potassium carbonate, sodium bicarbonate, potassium bicarbonate, sodium hydroxide, potassium hydroxide, lithium hydroxide, sodium acetate, and potassium acetate.

5. The method of claim 4, wherein a ratio of mole fractions of (2S,3R)-epoxy cinnamate represented by formula (III) to the compound represented by formula (VI) in step (2) is 1:(1.1-1.2), a ratio of mole fractions of the alkaline compound to (2S,3R)-epoxy cinnamate represented by formula (III) is 1:(0.1-1.0); a temperature of the amidation reaction is −20° C. to 40° C.; and a reaction time is 0.5 hours to 3 hours.

6. The method of claim 5, wherein a ratio of mole fractions of the compound represented by formula (VII) to the oxidant to ruthenium trichloride in step (3) is 1:(1-10):(0.03-1.0); a temperature of the oxidation reaction is −20° C. to 90° C.; and a reaction time is 0.5 hours to 24 hours.

7. The method of claim 6, wherein a solvent of the cyclization reaction in step (4) is an aqueous solution of the alkaline compound; in the aqueous solution, a mass percentage of the alkaline compound is 0.5%-5%; a temperature of the cyclization reaction is 10° C. to 90° C.; and a time of the cyclization reaction is 0.2 hours to 2 hours.

8. The method of claim 7, wherein step (1) and/or step (3) further comprise a step of adding an additive; the additive is at least one of phase transfer catalyst, an aqueous solution of disodium ethylenediamine tetraacetic acid, and an alkaline compound; wherein a disodium ethylenediamine tetraacetic acid is 0 to 0.001 mol/L, but not 0; the phase transfer catalyst is any one selected from a group consisting of benzyl triethyl ammonium chloride, tetrabutyl ammonium bromide, tetrabutyl ammonium chloride, tetrabutyl ammonium iodide, tetrabutyl ammonium bisulfate, trioctyl methyl ammonium chloride, dodecyl trimethyl ammonium chloride, and tetradecyl trimethyl ammonium chloride.

9. The method of claim 8, wherein a reductant of the reduction reaction in step (5) is sodium borohydride; a ratio of mole fractions of (−)-clausenamidone represented by formula (IX) to the reductant is 1:(1-2); a temperature of the reduction reaction is −20° C. to 40° C.; and a time of the reduction reaction is 0.5 hours to 3 hours.

10. The method of claim 9, wherein all of the solvents of the reactions in step (1), step (2), step (3), step (4), and step (5) are at least one selected from a group consisting of ethers solvent, alcohols solvent, esters solvent, halogenated alkanes solvent, $C_5$-$C_{10}$ alkanes solvent, amides solvent, nitriles solvent, and water; the ethers solvent is any one of ethyl ether, dipropyl ether, dibutyl ether, methyl t-butyl ether, 1,3-dioxane, 1,4-dioxane, tetrahydrofuran, dimethoxymethane, ethylene glycol monomethyl ether, ethylene glycol dimethyl ether, ethylene glycol monoethyl ether, ethylene glycol diethyl ether, and t-butyl methyl ether; the alcohols solvent is any one of methanol, ethanol, n-propyl alcohol, isopropyl alcohol, n-butyl alcohol, sec-butyl alcohol, t-butyl alcohol, and glycol; the esters solvent is any one of ethyl acetate, methyl acetate, propyl acetate, t-butyl acetate, and ethyl formate; the halogenated alkanes solvent is any one of dichloromethane, trichloromethane, and 1,2-dichloroethane; the $C_5$-$C_{10}$ alkanes solvent is any one of n-pentane, n-hexane, n-heptane, toluene, and dimethylbenzene; the amides solvent is N,N-dimethylformamide or N,N-dimethylacetamide; and the nitriles solvent is acetonitrile or propionitrile.

\* \* \* \* \*